US008790284B2

(12) United States Patent
Jeon et al.

(10) Patent No.: US 8,790,284 B2
(45) Date of Patent: Jul. 29, 2014

(54) WHEELCHAIR TYPE ROBOT FOR WALKING AID

(75) Inventors: Do Young Jeon, Seoul (KR); Hyo Sang Moon, Ahnyang-si (KR); Sin Ung Kwak, Seoul (KR); Jin Hwan Lee, Hwasung-si (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 717 days.

(21) Appl. No.: 13/125,567

(22) PCT Filed: Oct. 9, 2009

(86) PCT No.: PCT/KR2009/005782
§ 371 (c)(1),
(2), (4) Date: Apr. 21, 2011

(87) PCT Pub. No.: WO2010/047485
PCT Pub. Date: Apr. 29, 2010

(65) Prior Publication Data

US 2011/0201978 A1 Aug. 18, 2011

(30) Foreign Application Priority Data

Oct. 22, 2008 (KR) ........................ 10-2008-0103461

(51) Int. Cl.
*A61H 1/00* (2006.01)
*A61H 3/04* (2006.01)
*A61F 5/052* (2006.01)
*A61G 5/14* (2006.01)

(52) U.S. Cl.
USPC ............ 601/35; 601/5; 180/907; 297/DIG. 4; 297/DIG. 10

(58) Field of Classification Search
CPC ..... A61H 1/02; A61H 1/0237; A61H 1/0259; A61H 3/04; A61H 2003/04; A61H 2003/043; A61F 5/00; A61G 5/14; A61G 2200/36
USPC ........ 601/5, 33, 34, 35; 180/907; 297/DIG. 4, 297/DIG. 10
See application file for complete search history.

(56) References Cited

U.S. PATENT DOCUMENTS 3,964,786 A * 6/1976 Mashuda ...................... 297/330
4,054,319 A * 10/1977 Fogg et al. .................... 297/466

(Continued)

FOREIGN PATENT DOCUMENTS

JP 7163607 6/1995
JP 2007014698 1/2007

(Continued)

*Primary Examiner* — Justine Yu
*Assistant Examiner* — Christopher Miller
(74) *Attorney, Agent, or Firm* — IPLA P.A.; James E. Bame

(57) ABSTRACT

A wheelchair type robot for use as a walking aid wherein an outer skeleton to be worn on the lower body of a user is combined with a lift and a drive part in a wheelchair form. The drive part is furnished with a drive motor and wheels that are installed on a main frame. The lift is furnished with an outer linear guide that is fixed and joined with the main frame, an inner linear guide that can move up and down along same, an upper chair part that connects with the inner linear guide to enable up and down motion, and a lower chair part that connects with the outer linear guide such that unfolds if the inner linear guide descends and folds if it ascends. The outer skeleton is furnished with a lift locking part that is fixed and joined with the upper chair part, an upper frame whereto a thigh brace is joined, a lower frame whereto a calf brace is joined, a hip part that is installed between the lift locking part and the upper frame to rotate the upper frame around the lift locking part, and a knee joint part that is installed between the upper frame and the lower frame to rotate the lower frame around the upper frame.

9 Claims, 4 Drawing Sheets

(56) References Cited

U.S. PATENT DOCUMENTS

| | | | | |
|---|---|---|---|---|
| 4,067,249 | A * | 1/1978 | Deucher | 297/330 |
| 4,119,164 | A * | 10/1978 | Fogg et al. | 180/6.5 |
| 4,390,076 | A * | 6/1983 | Wier et al. | 180/11 |
| 4,456,086 | A * | 6/1984 | Wier et al. | 180/11 |
| 4,545,616 | A * | 10/1985 | Booth | 297/320 |
| 4,809,804 | A * | 3/1989 | Houston et al. | 180/65.51 |
| 5,096,008 | A * | 3/1992 | Mankowski | 180/6.5 |
| 5,137,102 | A * | 8/1992 | Houston et al. | 180/65.51 |
| 5,265,689 | A * | 11/1993 | Kauffmann | 180/65.51 |
| 5,366,036 | A * | 11/1994 | Perry | 180/65.1 |
| 5,701,968 | A * | 12/1997 | Wright-Ott et al. | 180/65.1 |
| 6,053,519 | A * | 4/2000 | Poindexter et al. | 280/250.1 |
| 6,203,106 | B1 * | 3/2001 | Nearing et al. | 297/329 |
| 6,231,067 | B1 * | 5/2001 | Johnson et al. | 280/650 |
| 6,250,717 | B1 * | 6/2001 | Porcheron | 297/411.3 |
| 6,440,046 | B1 * | 8/2002 | Tholkes | 482/142 |
| 6,601,869 | B2 * | 8/2003 | Porcheron | 280/648 |
| 7,036,512 | B2 * | 5/2006 | Harnois | 128/845 |
| 2003/0227161 | A1 * | 12/2003 | Redman et al. | 280/755 |
| 2004/0173998 | A1 * | 9/2004 | Meyer | 280/657 |
| 2004/0189071 | A1 * | 9/2004 | Komura et al. | 297/311 |
| 2006/0097557 | A1 * | 5/2006 | Tholkes et al. | 297/330 |
| 2010/0013276 | A1 * | 1/2010 | Tholkes et al. | 297/174 R |
| 2010/0207354 | A1 * | 8/2010 | Hunziker | 280/304.1 |

FOREIGN PATENT DOCUMENTS

| | | |
|---|---|---|
| JP | 2007181639 | 7/2007 |
| KR | 1020060039970 | 5/2006 |
| KR | 100716597 | 5/2007 |

* cited by examiner

WHEELCHAIR TYPE ROBOT FOR WALKING AID

BACKGROUND OF THE INVENTION

The present invention relates to a wheelchair type walking aid robot and, more particularly, to a wheelchair type walking aid robot in which a wheelchair type lift is combined with an exoskeleton designed for a user's lower body to enhance muscular strength or to help walking or rehabilitation.

Normally walking aids are used to assist patients or older people in their walking or rehabilitation. According to an increasing interest in the quality of life and welfare, and due to a rapid entry into an aging society, the research and development in walking aids show a tendency to increase.

Typical walking aids have a simple mechanism to operate depending on user's motion. However, recently introduced walking aids are attempting to combine a computer with a human engineering mechanism and thereby have some advantages such as better convenience and the effect of enhancing muscular strength. For instance, Korean Patent No. 612031 entitled 'Tendon-driven power assisting orthosis and control method' or Korean Patent No. 716597 entitled 'Robot for assistant exoskeletal power' discloses a technique that an exoskeleton is designed for a user's lower body and driven by a driving unit provided to an arm of a caster walker used as a walking aid.

Referring to FIG. 1, a conventional walking aid robot is composed of an exoskeleton 10 designed for a user's lower body, a caster walker 20 driven by a motor, and an arm 30 connecting the exoskeleton 10 and the caster walker 20. The exoskeleton 10 has a pair of leg frames 11 to which a hip joint part 12 and a knee joint part 13 are provided and with which a waist brace 14, a thigh brace 15 and a calf brace 16 are combined. The caster walker 20 with wheels 21 is driven by a separate driving motor and has a handle suitable for a user's grip. The arm 30 installed in the caster walker 20 and connected to the exoskeleton 10 has a driving assembly composed of a motor, a gear, etc. to respectively drive the hip joint part 12 and the knee joint part 13.

This conventional walking aid robot is very useful for rehabilitation through an increase of muscular strength as well as for a walking aid since the caster walker 20 drives by itself and also forces the driving assembly of the arm 30 to drive the hip joint part 12 and the knee joint part 13 of the exoskeleton 10.

Nevertheless, this conventional walking aid robot may be worth little as a long-range transportable means because it fails to have a driving function of existing wheelchair.

Also, the conventional walking aid robot has a considerably great turning radius due to limitations on degree of freedom, so it may be not available in a narrow space.

Additionally, the conventional walking aid robot has a great possibility of overturning or of causing a user to fall down when it fails to work correctly or when a user loses balance. Therefore, it may be weak in structural stability.

Furthermore, the conventional walking aid robot that assists user's motion by applying a torque to each joint part may often fail to offer 100 percent power in case of user's sitting or rising actions due to limitations on torque output of a driving motor.

SUMMARY OF THE INVENTION

The present invention is to provide a wheelchair type walking aid robot that has a driving function in addition to a walking aid and rehabilitation function.

Also, the present invention is to provide a wheelchair type walking aid robot that can reduce restrictions on a usable space.

Also, the present invention is to provide a wheelchair type walking aid robot that improves structural stability and promotes convenience in use.

Also, the present invention is to provide a wheelchair type walking aid robot that can offer 100 percent power necessary for user's sitting or rising actions.

Accordingly, the present invention is to address the above-mentioned problems and/or disadvantages and to offer at least the advantages described below.

According to one aspect of the present invention, provided is a wheelchair type walking aid robot comprising a driving unit, a lift, and an exoskeleton. The driving unit includes a main frame, a driving motor provided to the main frame, and wheels provided to the main frame and driven by the driving motor. The lift includes an outer linear guide fixed to the main frame, an inner linear guide capable of a vertical movement along the outer linear guide, an upper chair part connected to the inner linear guide and capable of a vertical movement, and a lower chair part connected to the outer linear guide wherein the lower chair part is unfolded or folded when the inner linear guide descends or ascends. The exoskeleton includes a lift locking part combined with the upper chair part, an upper frame having a thigh brace joined thereto, a lower frame having a calf brace joined thereto, a hip joint part installed between the lift locking part and the upper frame and forcing the upper frame to rotate with respect to the lift locking part, and a knee joint part installed between the upper frame and the lower frame and forcing the lower frame to rotate with respect to the upper frame.

In the wheelchair type walking aid robot, the lift may further include a linear actuator fixed to the main frame, connected to the inner linear guide, and vertically driving the inner linear guide.

Also, in the wheelchair type walking aid robot, the lift may further include an outer link block fixedly connected to the inner linear guide and movably connected to the outer linear guide.

Also, in the wheelchair type walking aid robot, the lift may further include an inner link block fixedly connected to the upper chair part and movably connected to the inner linear guide.

Also, in the wheelchair type walking aid robot, the lift may further include a sprocket provided to an upper end of the inner linear guide, and a chain connected at one end to the main frame, traveling on the sprocket, and connected at the other end to the inner link block, and wherein when the inner link block moves upwards along the inner linear guide by the chain, the upper chair part moves upwards together.

Also, in the wheelchair type walking aid robot, the lift may further include a rack gear formed on the outer linear guide, a first spur gear engaged with the rack gear and inserted into the outer link block to run idle, and a second spur gear engaged with the first spur gear and having the shaft fixed to the lower chair part, and wherein when the outer link block rises by the inner linear guide, the lower chair part is folded downwards.

Also, in the wheelchair type walking aid robot, the lift may further include a waist brace provided to the upper chair part.

Also, in the wheelchair type walking aid robot, the exoskeleton may further include a hip joint driving member provided to both ends of the lift locking part and offering a rotating force to the hip joint part.

Also, in the wheelchair type walking aid robot, the exoskeleton may further include a knee joint driving member provided directly to the knee joint part and offering a rotating force to the knee joint part.

By combining an exoskeleton designed for the purpose of walking aid and rehabilitation, a wheelchair shaped lift, and a driving unit, the present invention maximizes user's convenience and mechanical efficiency. Namely, due to excellent mobility, a wheelchair type walking aid robot of this invention can be usefully used as a transportable means.

Also, by further realizing a wheelchair function, a wheelchair type walking aid robot of this invention can operate like a wheelchair with a higher degree of freedom in a narrow space, thereby reducing restrictions on a usable space and widening user's activity areas.

Furthermore, a wheelchair type walking aid robot of this invention not only has good structural stability since the center of mass lies in the middle of a wheelchair, but also can enhance the stability in sitting or rising actions and offer enough torque by employing a lift.

DETAILED DESCRIPTION OF THE INVENTION

Exemplary, non-limiting embodiments of the present invention will now be described more fully with reference to the accompanying drawings. This invention may, however, be embodied in many different forms and should not be construed as limited to the exemplary embodiments set forth herein. Rather, the disclosed embodiments are provided so that this disclosure will be thorough and complete, and will fully convey the scope of the invention to those skilled in the art. The principles and features of this invention may be employed in varied and numerous embodiments without departing from the scope of the invention.

Furthermore, well known or widely used techniques, elements, structures, and processes may not be described or illustrated in detail to avoid obscuring the essence of the present invention. Although the drawings represent exemplary embodiments of the invention, the drawings are not necessarily to scale and certain features may be exaggerated or omitted in order to better illustrate and explain the present invention.

Figure 1:
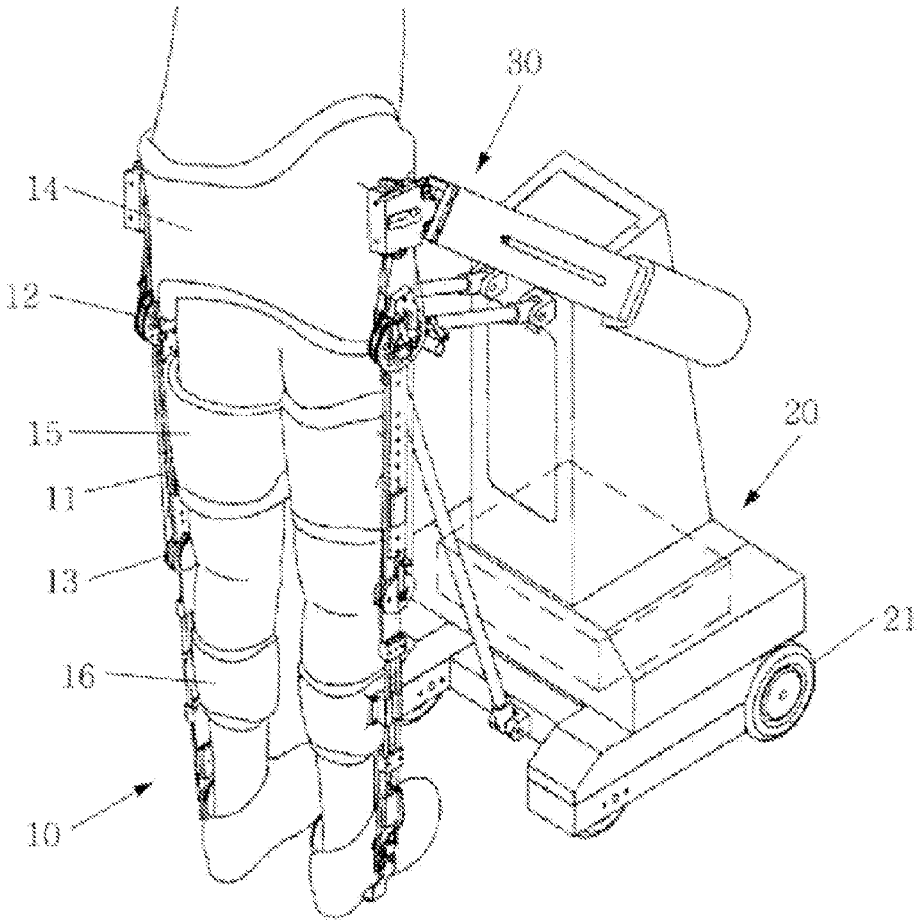
FIG. 1 Prior Art
FIG. 1 shows a using state of a conventional walking aid robot.
Figure 2:
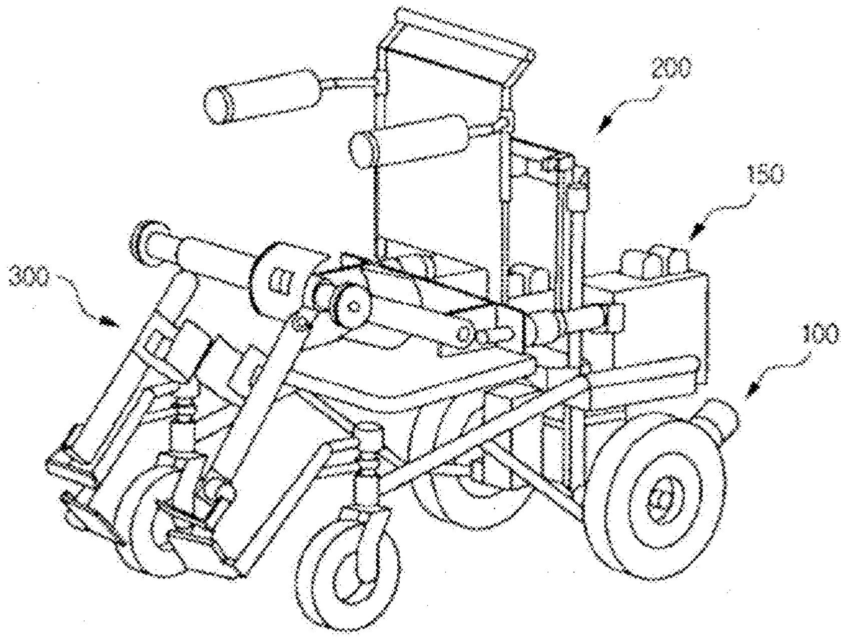
FIG. 2 is a perspective view illustrating a wheelchair type walking aid robot in accordance with an exemplary embodiment of the present invention.
Figure 3:
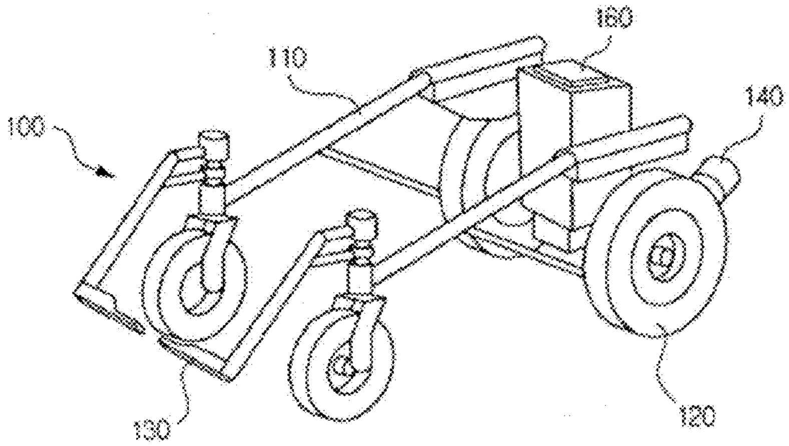
FIG. 3 is a perspective view illustrating a driving unit of the wheelchair type walking aid robot shown in FIG. 2.
Figure 4:
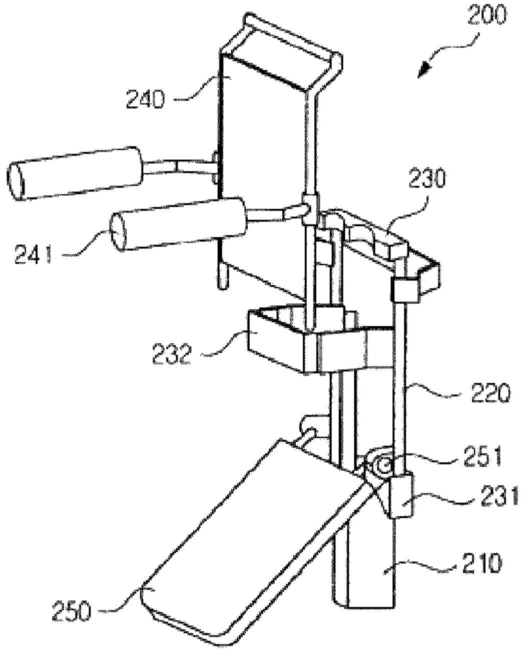
FIG. 4 is a perspective view illustrating a lift of the wheelchair type walking aid robot shown in FIG. 2.
Figure 5:
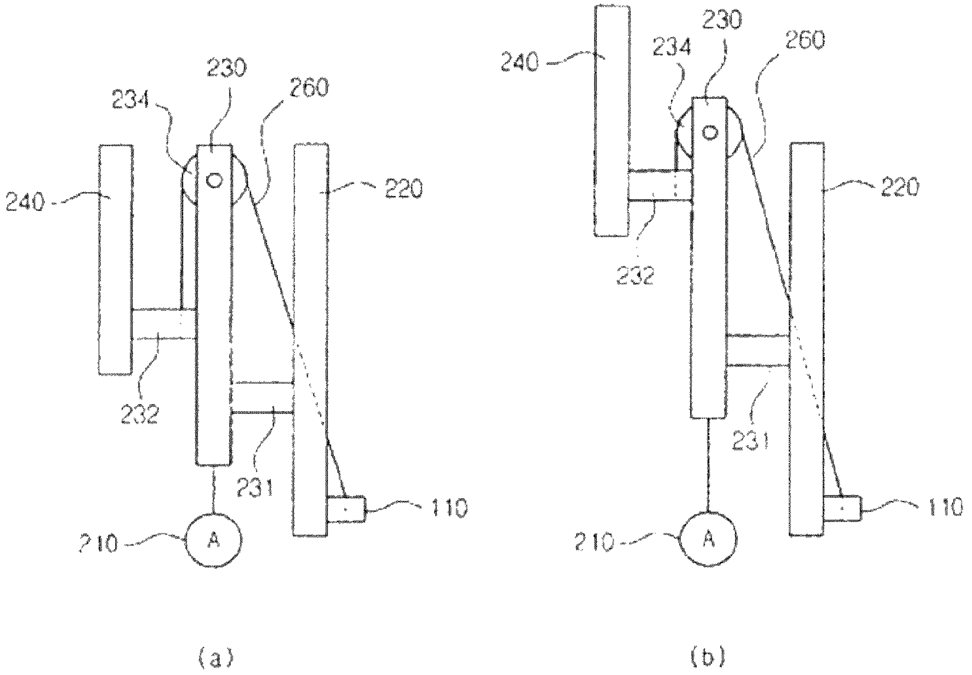
FIGS. 5 and 6 illustrate the operation mechanism of the lift shown in FIG. 4.
Figure 6:
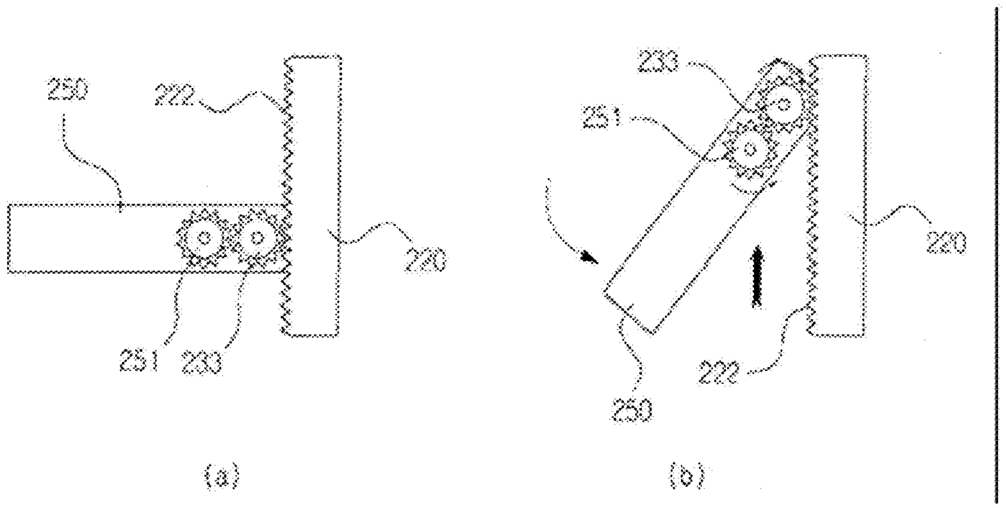
Figure 7:
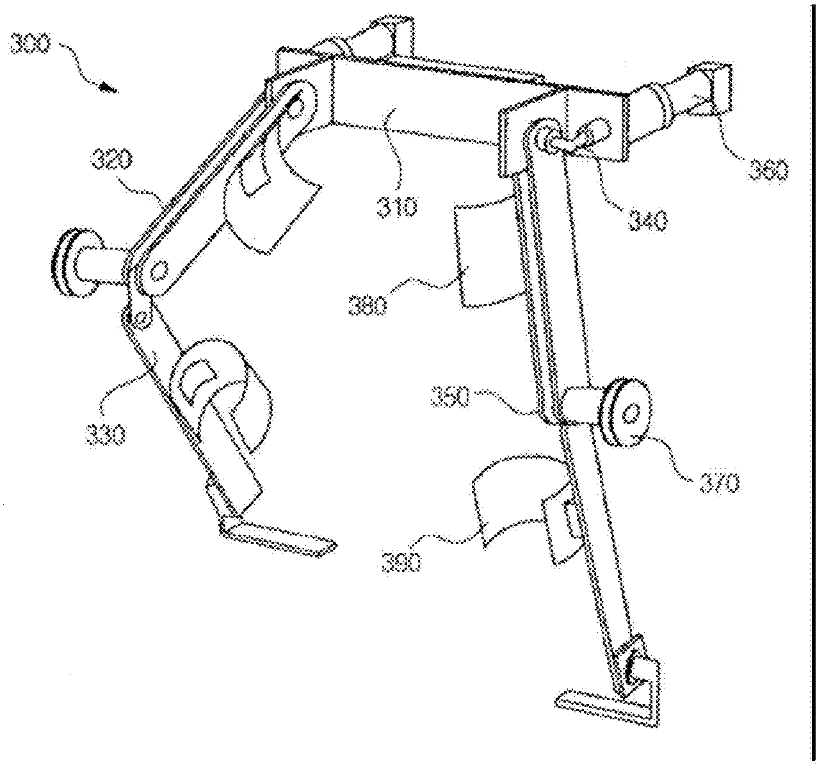
FIG. 7 is a perspective view illustrating an exoskeleton of the wheelchair type walking aid robot shown in FIG. 2.

FIG. 2 is a perspective view illustrating a wheelchair type walking aid robot in accordance with an exemplary embodiment of the present invention. Referring to FIG. 2, the wheelchair type walking aid robot includes a driving unit 100, a lift 200, and an exoskeleton 300. The driving unit 100 is shown in FIG. 3, the lift 200 is shown in FIGS. 4 to 6, and the exoskeleton 300 is shown in FIG. 7.

Now, the driving unit of the wheelchair type walking aid robot will be described with reference to FIGS. 2 and 3. The driving unit 100 is composed of a main frame 110, wheels 120, a footrest 130, a driving motor 140, a controller 150, and a battery 160.

The main frame 110 forms the framework of the driving unit 100 and also gives the groundwork for the other elements of the driving unit 100. Additionally, as will be described later, the main frame 110 is combined with the lift 200 and also offers a supporting force to the lift 200.

The wheels 120 have a pair of front wheels and a pair of rear wheels. The rear wheels are directly driven by the driving motor 140, and the front wheels are casters that freewheel. Namely, the driving unit 100 of this invention adopts a rear-driven type and thereby increases full power.

The footrest 130 is connected to the front end of the main frame 110 and also gives a support on which a user who sits on a chair of the lift 200 rests his or her feet.

The driving motor 140 is provided to the rear end of the main frame 110 and also supplies a driving force to the rear wheels.

The controller 150 is provided to the rear end of the main frame 110 and controls the driving motor 140 of the driving unit 100. In addition, the controller 150 may further control a linear actuator of the lift 200 or joint driving members of the exoskeleton 300 to be described later. Normally the controller 150 separately and selectively drives the driving motor 140, the linear actuator and the joint driving members when a user uses driving function or walking-aid function of the wheelchair type robot. The controller 150 is omitted in FIG. 3 for clarity of illustration.

The battery 160 is provided to the rear end of the main frame 110 and also respectively supplies electric power to the driving motor 140 of the driving unit 110, the linear actuator of the lift 200, and the joint driving members of the exoskeleton 300.

Now, the lift of the wheelchair type walking aid robot will be described with reference to FIGS. 2, 4 to 6. The lift 200 is composed of a linear actuator 210, an outer linear guide 220, an inner linear guide 230, an upper chair part 240, a lower chair part 250, and a chain 260.

The linear actuator 210 is fixed to the main frame 110 of the driving unit 100. Also, the linear actuator 210 is connected to the inner linear guide 230 and vertically drives the inner linear guide 230. Although FIG. 5 shows the linear actuator 210 connected to a lower end of the inner linear guide 230, this is exemplary only and not to be considered as a limitation of the invention. Alternatively, the linear actuator 210 may be located near the lower end of the inner linear guide 230 but connected to an upper end of the inner linear guide 230 through an additional connection rod.

Like the linear actuator 210, the outer linear guide 220 is fixed to the main frame 110 of the driving unit 100. Also, the outer linear guide 220 has a rack gear 222, which will be described later with reference to FIG. 6.

The inner linear guide 230 is connected to the linear actuator 210 as mentioned above and moves in a vertical direction. Additionally, the inner linear guide 230 is connected to the outer linear guide 220 through an outer link block 231 and connected to the upper chair part 240 through an inner link block 232. Particularly, as understood from the operation mechanism of the lift shown in FIG. 5, the outer link block 231 is fixedly connected to the inner linear guide 230 and movably connected to the outer linear guide 220. Also, the inner link block 232 is fixedly connected to the upper chair part 240 and movably connected to the inner linear guide 230. Meanwhile, the shaft of the first spur gear 233 shown in FIG. 6 is inserted into the outer link block 231 to run idle, and a sprocket 234 is provided to an upper end of the inner linear guide 230. Further discussion related to the inner linear guide 230 will be made later with reference to FIGS. 5 and 6.

The upper chair part 240 (i.e., backrest) is connected to the inner linear guide 230 through the inner link block 232 as mentioned above. Additionally, the upper chair part 240 has an armrest 241. The movement of the upper chair part 240 will be described later with reference to FIG. 5.

The lower chair part 250 is fixedly connected to the shaft of the second spur gear 251. As shown in FIG. 6, the second spur gear 251 is engaged with the first spur gear 233 of the outer link block 231. The lower chair part 250 and the spur gears 233 and 251 will be described later with reference to FIG. 6.

As shown in FIG. 5, the chain 260 is connected at one end to the main frame 110 of the driving unit (100 in FIG. 3), travels on the sprocket 234 of the inner linear guide 230, and is connected at the other end to the inner link block 232. The chain 260 may be replaced with any other equivalent such as a wire, and accordingly the sprocket 234 may be replaced with a pulley or the like. In some cases, the chain 260 and the sprocket 234 may not be used. In these cases, the upper chair part 240 is fixedly connected to the inner linear guide 230 through the inner link block 232.

Although not illustrated in the drawings, the lift 200 may further have a waist brace provided to the upper chair part 240.

Now, the operation mechanism of the lift 200 will be described through FIGS. 5 and 6.

On one hand, referring to FIG. 5, when the linear actuator 210 drives the inner linear guide 230 upwards with the outer linear guide 220 fixed, the inner linear guide 230 moves upwards along the outer linear guide 220 together with the outer link block 231. At this time, one end of the chain 260 is bound to the main frame 110, so a binding location of the chain 260 is fixed. Therefore, as the inner linear guide 230 rises, the sprocket 234 rotates and thereby draws the other end of the chain 260 connected to the inner link block 232. As a result, the inner link block 232 moves upwards along the inner linear guide 230 by the chain 260, and also the upper chair part 240 fixed to the inner link block 232 moves upwards.

On the other hand, referring to FIG. 6, the rack gear 222 is formed on one side of the outer linear guide 220, and the first spur gear 233 is engaged with the rack gear 222. Even though not illustrated in the drawings, the first spur gear 233 is inserted into the outer link block 231 and runs idle. The first and second spur gears 233 and 251 are engaged with each other, and the shaft of the second spur gear 251 is fixed to the lower chair part 250. Therefore, when the inner linear guide 230 rises, the outer link block 231 as well moves upwards, and further the first spur gear 233 connected to the outer link block 231 moves upwards along the rack gear 222 while rotating by means of the rack gear 222. Additionally, the second spur gear 251 engaged with the first spur gear 233 rotates in the opposite direction to the first spur gear 233 and rises. Therefore, the lower chair part 250 to which the shaft of the second spur gear 251 is fixed rotates as folded downwards.

Briefly, while the upper chair part 240 is located at a lower level and the lower chair part 250 is unfolded, a user can sit on a chair and use a wheelchair function. However, when a user rises from the chair, the upper chair part 240 moves upwards, and the lower chair part 250 is folded backwards so as not to disturb a user's upright or walk.

Now, the exoskeleton of the wheelchair type walking aid robot will be described with reference to FIGS. 2 and 7. The exoskeleton 300 is designed for a user's lower body and helps user's walking motion or sitting/rising actions. The exoskeleton 300 is composed of a lift locking part 310, an upper frame 320, a lower frame 330, a hip joint part 340, a knee joint part 350, a hip joint driving member 360, a knee joint driving member 370, a thigh brace 380, and a calf brace 390.

The lift locking part 310 is combined with the upper chair part 240 of the lift 200. Therefore, when the upper chair part 240 rises, the lift locking part 310 as well moves upwards.

A pair of the upper frames 320 corresponds to user's thighs, and a pair of the lower frames 330 corresponds to user's calves. Additionally, a pair of the hip joint parts 340 corresponds to user's hip joints, and a pair of the knee joint parts 350 corresponds to user's knee joints.

The hip joint part 340 is installed between the lift locking part 310 and the upper frame 330. The hip joint driving member 360 is provided to both ends of the lift locking part 310 and offers a rotating force to the hip joint part 340. The hip joint driving member 360 may be formed of a motor, a motor shaft, a bevel gear, or any other power transmission manners. The hip joint part 340 rotates by means of the hip joint driving member 360, and therefore the upper frame 320 rotates with respect to the lift locking part 310 so as to realize user's walking motion or sitting/rising actions.

The knee joint part 350 is installed between the upper frame 320 and the lower frame 330. The knee joint driving member 370 is provided directly to the knee joint part 350 and offers a rotating force to the knee joint part 350. The knee joint driving member 370 may be formed of a motor, a motor shaft, or any other power transmission manners. The knee joint part 350 rotates by means of the knee joint driving member 370, and therefore the lower frame 330 rotates with respect to the upper frame 330 so as to realize user's walking motion or sitting/rising actions.

The thigh brace 380 and the calf brace 390 a user wears are joined to the upper frame 320 and the lower frame 330, respectively.

While this invention has been particularly shown and described with reference to an exemplary embodiment thereof, it will be understood by those skilled in the art that various changes in form and details may be made therein without departing from the spirit and scope of the invention as defined by the appended claims.

What is claimed is:

1. A wheelchair walking aid robot comprising:

a driving unit including a main frame, a driving motor provided to the main frame, and wheels provided to the main frame and driven by the driving motor;

a lift including an outer linear guide fixed to the main frame, an inner linear guide capable of a vertical movement along the outer linear guide, an upper chair part connected to the inner linear guide and capable of a vertical movement, and a lower chair part directly connected to the outer linear guide wherein the lower chair part is unfolded or folded when the inner linear guide descends or ascends, respectively; and an exoskeleton including a lift locking part combined with the upper chair part, an upper frame having a thigh brace joined to the upper frame, a lower frame having a calf brace joined to the lower frame, a hip joint part installed between the lift locking part and the upper frame and forcing the upper frame to rotate with respect to the lift locking part, and a knee joint part installed between the upper frame and the lower frame and forcing the lower frame to rotate with respect to the upper frame.

2. The wheelchair walking aid robot of claim 1, wherein the lift further includes a linear actuator fixed to the main frame, connected to the inner linear guide, and vertically driving the inner linear guide.

3. The wheelchair walking aid robot of claim 1, wherein the lift further includes an outer link block fixedly connected to the inner linear guide and movably connected to the outer linear guide.

4. The wheelchair walking aid robot of claim 1, wherein the lift further includes an inner link block fixedly connected to the upper chair part and movably connected to the inner linear guide.

5. The wheelchair walking aid robot of claim 4, wherein the lift further includes a sprocket provided to an upper end of the inner linear guide, and a chain connected at one end to the main frame, traveling on the sprocket, and connected at the other end to the inner link block, and wherein when the inner link block moves upwards along the inner linear guide by the chain, the upper chair part moves upwards together.

6. The wheelchair walking aid robot of claim 3, wherein the lift further includes a rack gear formed on the outer linear guide, a first spur gear engaged with the rack gear and inserted into the outer link block to run idle, and a second spur gear engaged with the first spur gear and having a shaft of the first spur gear fixed to the lower chair part, and wherein when the outer link block rises by the inner linear guide, the lower chair part is folded downwards.

7. The wheelchair walking aid robot of claim 1, wherein the lift further includes a waist brace provided to the upper chair part.

8. The wheelchair walking aid robot of claim 1, wherein the exoskeleton further includes a hip joint driving member provided to both a first end and a second end of the lift locking part and offering a rotating force to the hip joint part.

9. The wheelchair walking aid robot of claim 1, wherein the exoskeleton further includes a knee joint driving member provided directly to the knee joint part and offering a rotating force to the knee joint part.

* * * * *